United States Patent
Holland (10) Patent No.: US 11,103,645 B2
(45) Date of Patent: Aug. 31, 2021

(54) SYRINGE AND PISTON ROD WITH GASKET ENGAGING PORTION

(71) Applicant: OWEN MUMFORD LTD, Oxfordshire (GB)

(72) Inventor: Damian Alexander Holland, Oxfordshire (GB)

(73) Assignee: Owen Mumford Limited, Oxford (GB)

(*) Notice: Subject to any disclaimer, the term of this patent is extended or adjusted under 35 U.S.C. 154(b) by 159 days.

(21) Appl. No.: 16/336,785

(22) PCT Filed: Sep. 21, 2017

(86) PCT No.: PCT/GB2017/052833
§ 371 (c)(1),
(2) Date: Mar. 26, 2019

(87) PCT Pub. No.: WO2018/060682
PCT Pub. Date: Apr. 5, 2018

(65) Prior Publication Data
US 2019/0224421 A1   Jul. 25, 2019

(30) Foreign Application Priority Data
Sep. 27, 2016 (GB) ...................... 1616398

(51) Int. Cl.
*A61M 5/315* (2006.01)

(52) U.S. Cl.
CPC .............. *A61M 5/31515* (2013.01); *A61M 2005/31521* (2013.01); *A61M 2005/31523* (2013.01)

(58) Field of Classification Search
CPC .... A61M 5/31515; A61M 2005/31516; A61M 5/31513; A61M 2005/31521; A61M 5/31501; A61M 2005/31523
See application file for complete search history.

(56) References Cited

U.S. PATENT DOCUMENTS

| 4,180,069 A | 12/1979 | Walters |
| 5,980,487 A * | 11/1999 | Jones ................ A61M 5/31511 604/110 |

(Continued)

FOREIGN PATENT DOCUMENTS

| CN | 100430103 C | 11/2008 |
| CN | 101743026 A | 6/2010 |

(Continued)

OTHER PUBLICATIONS

International Search Report, dated Dec. 19, 2017, from corresponding PCT/GB2017/052833 application.

(Continued)

*Primary Examiner* — Bhisma Mehta
*Assistant Examiner* — John J Crawford
(74) *Attorney, Agent, or Firm* — Quarles & Brady LLP (57) ABSTRACT

A plunger rod for use in a syringe barrel for driving a bung through the syringe barrel to expel a substance therefrom, the plunger rod including: a bung fixing configured to be received within a recess of a bung and including at least one laterally extending lug including a thread engagement surface configured to engage with a point on a track portion of a thread on a sidewall of the recess, wherein the lug is further configured to cross the thread on relative rotation between the plunger rod and the bung under a force applied by a user, such that the thread engagement surface of the lug engages the point of the track portion every full rotation of the syringe plunger relative to the bung.

17 Claims, 5 Drawing Sheets

(56) References Cited

U.S. PATENT DOCUMENTS

2012/0184920 A1     7/2012   Okihara et al.
2016/0089499 A1*   3/2016   Okuda ................ A61M 5/3129
                                                                             604/222

FOREIGN PATENT DOCUMENTS

| CN | 102639174 A | 8/2012 |
|----|-------------|--------|
| CN | 104941039 A | 9/2015 |
| CN | 103301535 B | 10/2015 |
| JP | 10500324 A | 1/1998 |
| JP | 2002272843 A | 9/2002 |
| JP | 2011182944 A | 9/2011 |
| WO | 0197885 A1 | 12/2001 |
| WO | 2011040522 A1 | 4/2011 |
| WO | 2014196056 A1 | 12/2014 |

OTHER PUBLICATIONS

GB Search Report, dated Mar. 20, 2017, from corresponding GB 1616398.2 application.
Taiwanese Office Action from corresponding Taiwanese Patent Application No. 106132957, dated Dec. 21, 2020 (20 pages) (English translation included).
First Office Action from corresponding Chinese Patent Application No. 201780059011.9, dated Dec. 24, 2020 (11 pages).
Office Action from corresponding Japanese Patent Application No. 2019-511527, dated Apr. 19, 2021 (9 pages) (English translation included).

* cited by examiner

SYRINGE AND PISTON ROD WITH GASKET ENGAGING PORTION

TECHNICAL FIELD

The invention relates to a plunger rod for use with syringes. In some arrangements, the invention may relate to a plunger for use with a syringe and/or to syringes comprising the plunger and/or plunger rod. The invention may relate to, but need not be limited to, safety syringes.

BACKGROUND

Typically, a plunger rod places a resiliently deformable bung in compression in at the end of a barrel of the syringe in order to ensure full drug delivery. In some syringe designs this can lead to problems relating to the force exerted by the bung on the plunger rod to push the plunger rod outwards.

SUMMARY

The inventors have appreciated that in order to alleviate problems caused by the bung forcing the plunger rod outwards, it is desirable that the bung remains under compression and/or that energy stored in the bung when it is compressed is not permitted to force the plunger rod outwards from a barrel of the syringe.

According to an aspect of the invention, there is provided a plunger rod for use in a syringe barrel for driving a bung through the syringe barrel to expel a substance therefrom, the plunger rod comprising: a bung fixing configured to be received within a recess of a bung and comprising at least one laterally extending lug comprising a thread engagement surface configured to engage with a point on a track portion of a thread on a sidewall of the recess, wherein the lug is further configured to cross the thread on relative rotation between the plunger rod and the bung under a force applied by a user, such that the thread engagement surface of the lug engages the point of the track portion every full rotation of the syringe plunger relative to the bung.

Optionally, the at least one lug is configured to act upon the track portion of the thread before crossing the thread.

Engagement with the track portion of the thread encompasses the one or more lugs being in contact with the track portion. The engagement may be neutral in that there need not be any translation of torque applied to the plunger rod into a linear force acting on the thread. When the one or more lugs are engaged with the thread they may apply linear force from the plunger rod to the bung. Acting upon the track portion encompasses the one or more lugs being engaged with the thread and also translating a torque applied to the thread into linear force acting on the bung. If a bung is under compression then the lugs are able to act on the thread to alter the distribution of and/or release energy stored within the bung such that the plunger rod is not forced outwards. After the lug crosses the thread, the compression of the bung may return to a normal state of distribution wherein the energy stored in the compressed bung forces the plunger rod outwards. Therefore, the lugs are configured to prevent the plunger rod from being forced outwards at specific points on rotation of the plunger rod by engaging with and/or acting on the thread.

Optionally, the plunger rod further comprises a plurality of lugs angularly spaced about a periphery of the bung fixing such that the thread engagement surface of each of the plurality of lugs engages the point of the track portion of the thread at a corresponding angle of rotation of the plunger rod.

Optionally, the plurality of lugs are equally angularly spaced.

Optionally, first and second lugs are on opposite sides of the bung fixing.

Optionally, the first and second lugs are configured such that when the thread engagement surface of the first lug is engaged with the point on the track portion, the thread engagement surface of the second lug engages a point on a further track portion opposite to the track portion.

Optionally, each of the lugs is at the same longitudinal position on the plunger rod.

Optionally, the thread engagement surface of the at least one lug is angled to allow linear motion of the at least one lug through the thread.

Optionally, the plunger rod further comprises a shoulder configured to abut a surface of the bung surrounding the recess when the bung fixing is received therein, the shoulder being configured to resist further longitudinal movement of the plunger rod into the recess.

Optionally, an extension of the bung fixing from the shoulder is such that when the shoulder abuts the surface of the bung surrounding the recess, the bung fixing is not in contact with a bottom surface of the recess.

Optionally, the at least one lug is configured to act on the thread to compress a portion of the bung between the at least one lug and the shoulder.

Optionally, a keyed portion of the plunger rod has a non-circular cross section configured to engage a corresponding keyed aperture of a syringe to prevent rotation of the plunger rod, and wherein the at least one lug is positioned such that the thread engagement surface engages the point of the track portion of the thread when the cross section of the plunger rod is aligned with the keyed aperture.

Optionally, the lug is positioned such that it acts upon the track portion of the thread when the cross section of the plunger rod is aligned with the keyed aperture.

According to an aspect of the invention, there is provided a plunger comprising: a plunger rod as described herein, and a bung comprising a recess and an internal thread on a sidewall of the recess, wherein the bung fixing of the plunger rod is received within the recess of the bung.

According to an aspect of the invention, there is provided a syringe comprising: a plunger/plunger rod as described herein.

Optionally, the plunger rod may be received within a mouth of a barrel of the syringe such that movement of the plunger within the barrel expels a substance therefrom, wherein the mouth of the barrel comprises a keyed aperture corresponding to the non-circular cross section of the keyed portion of the plunger rod and configured to engage therewith to prevent rotation of the plunger rod relative to the barrel, and wherein, after the keyed portion of the plunger rod has passed through the aperture, the plunger rod is rotatable relative to the barrel and the bung.

Optionally, the bung is resiliently deformable and the plunger rod is configured to compress the bung against an end of the barrel as the keyed portion of the plunger rod passes through the keyed aperture in the mouth of the barrel, such that during rotation of the plunger, energy is stored in the bung and exerts a force on the plunger rod outwards from the barrel.

Optionally, the thread engagement surface of the at least one lug of the plunger rod is configured to engage the point on the track portion of the thread on the sidewall of the bung when the keyed portion of the plunger rod is aligned with the keyed aperture, such that the bung does not expand to force the plunger rod out of the aperture.

Optionally, the at least one lug is configured to act upon the track portion of the thread on the sidewall of the bung to compress a portion of the bung between the at least one lug and the shoulder of the plunger rod when the keyed portion of the plunger rod is aligned with the keyed aperture.

BRIEF DESCRIPTION OF THE DRAWINGS

Exemplary embodiments of the invention are disclosed herein with reference to the accompanying drawings, in which:

FIGS. 6a-c show a longitudinal section through a needle end of a syringe showing a plunger at various stages of operation; and FIGS. 6aa-cc show lateral sections through a needle end of a syringe corresponding to FIGS. 6a-c.

DETAILED DESCRIPTION

Generally disclosed herein are exemplary plunger rods for use in syringes, wherein the plunger rods are configured to hold a bung in compression at an end of a barrel of the syringe and/or to redistribute energy stored within the bung to prevent the plunger rod being forced outwards. In exemplary methods and apparatus the plunger rod may be configured to pass through a keyed aperture in the syringe and then to rotate after it has passed through. In such arrangements, the rotation of the plunger rod may bring it into alignment with the keyed aperture at one or more points during rotation and the plunger rods are configured to prevent the bung from driving the plunger rods back through the keyed aperture at these alignment points. The redistribution of energy stored in a bung may encompass a change in the amount of compression of one or more portions of the bung.

The term "inward" when applied to the stroke of a plunger encompasses movement of the plunger longitudinally within a syringe barrel and towards an opening in the end of the syringe barrel, typically fitted with a needle. That is, in a direction to expel a substance from the barrel. The term "outward" when applied to the stroke has the opposite meaning, the movement of the plunger out of the barrel.

Exemplary plunger rods comprise at least one lug configured to engage with a point on a track portion of a thread of a bung. The at least one lug may be configured to cross the thread of the bung on rotation of the plunger rod. That is, the lug may cross into adjacent track portions of the thread. The lug and/or the bung are configured such that a predetermined torque is required for the lug to cross the thread. The predetermined torque may be such that the lug acts upon the thread for a time before crossing the thread. The point at which the lug acts on the thread may be configured to coincide with the point at which the plunger rod is aligned with the keyed aperture, as explained in detail below. In this way, the plunger rod does not screw into the bung, although it may use a force generated by the lug acting upon the bung. In exemplary syringe plungers the engagement of the at least one lug with the point on the track portion of the thread of the bung holds the bung in a compressed state and/or prevents expansion of the bung to drive the plunger rod outwards.

Figure 1A:
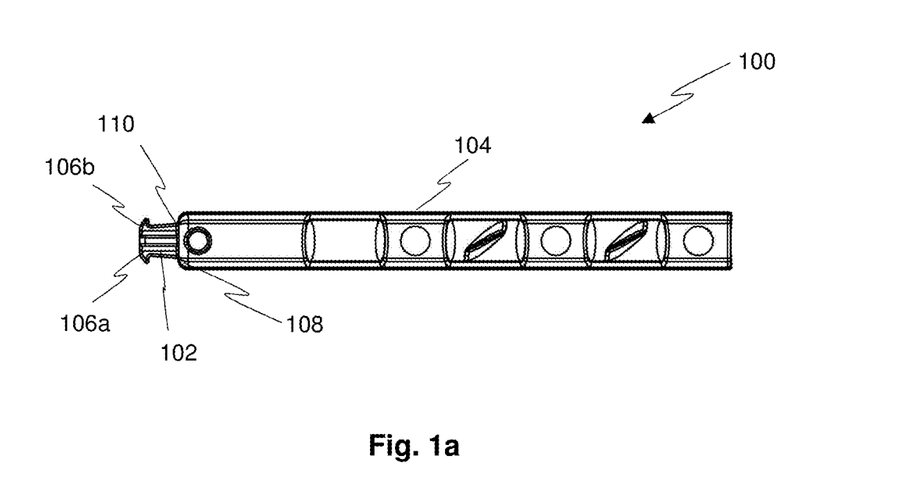
FIG. 1 is a front view of a plunger rod.
Figure 1B:
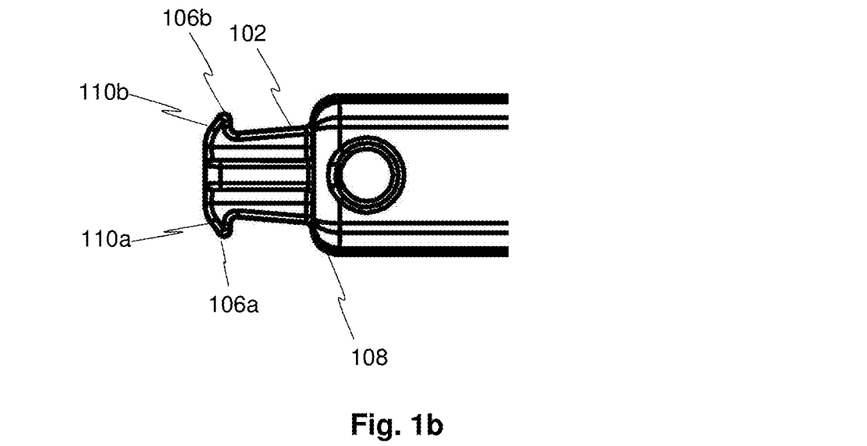

FIGS. 1a and 1b show an exemplary plunger rod 100 comprising a first end 102 and a plunger shaft 104. FIG. 1b shows an enlarged view of a first end 102 of a plunger rod 100. The first end 102 comprises a plurality of laterally extending lugs 106a-b.

As used herein, the term "lateral" encompasses a direction transverse to a longitudinal axis of the plunger rod. More generally, relative terms such as lateral, longitudinal, upper, lower etc. are used herein to aid description and need not be limiting on the scoped of the invention.

The first end 102, also termed a bung fixing, of the plunger rod 100 is configured to be received by a recess of a bung to form a plunger, as discussed below. The combination of the plunger rod 100 and the bung is referred to throughout this document as a plunger.

The bung fixing 102 has a substantially circular cross section and tapers in a direction away from a shoulder 108 of the plunger rod 100 towards the end of the bung fixing 102. The bung fixing 102 of the plunger rod 100 comprises a plurality of lugs 106a-b extending laterally therefrom. In the exemplary plunger rod 100 of FIGS. 1a and 1b, the lugs 106a-b are located at the extremity of the bung fixing 102, however the lugs 106a-b may alternatively be located at any other points along the first end 102. The exemplary syringe plunger 100 of FIGS. 1a and 1b comprises two opposed lugs 106a, 106b. That is, the lugs 106a, 106b extend in opposite directions from the bung fixing 102. As the bung fixing 102 has a substantially circular cross section, the lugs 106a, 106b may be considered diametrically opposite. However, it should be understood that other exemplary syringe plungers may comprise another number of lugs of various angular spacings.

Each of the lugs 106a-b extends laterally from the same point on the longitudinal axis of the plunger rod 100. As such, in exemplary plunger rods 100, the distance between the shoulder 108 and each of the plurality of lugs 106a, 106b may be substantially equal. In other arrangements, the lugs may extend from different positions on the longitudinal axis of the plunger rod 100.

The lugs 106a, 106b comprise a thread engagement surface 110a, 110b. The thread engagement surfaces 110a, 110b is configured to contact a thread of the bung and are angled rearwards from a plane perpendicular to the longitudinal axis of the plunger rod 100. The thread engagement surfaces 110a, 110b are at an angle in a range from 30 degrees to 40 degrees to a lateral axis extending perpendicularly from the longitudinal axis of the plunger rod 100. In a specific arrangement, the thread engagement surfaces 110a, 110b are at an angle of 36 degrees to the lateral axis. The angled thread engagement surfaces 110a, 110b are configured to allow the bung fixing of the plunger rod 100 to be driven linearly into the bung by overcoming the thread.

A distance between the lateral outer limits of the lugs 106a, 106b may be in a range from 3 mm to 4 mm and in a specific arrangement may be 3.8 mm. The lateral extension of each lug 106a, 106b may be in a range from 0.5 mm to 1 mm and in a specific example may be 0.6 mm. The lugs may have a width in a range from 0.5 mm to 1 mm. The lugs 106a, 106b may extend perpendicular to the plunger rod 100 and in certain exemplary arrangements the thread engagement surface is not aligned with the angle of the thread of the bung. The lugs 106a, 106b may be manufactured from a rigid plastics material.

The shoulder 108 is curved and is configured to abut a surface of the bung, as described below. A distance from the shoulder 108 to an upper surface of the lugs 106a, 106b may be in a range from 2 mm to 3 mm and in a specific arrangement may be 2.5 mm.

An internal diameter of a threaded recess of a bung configured to cooperate with the plunger rod 100, may be in a range from 2 mm to 3 mm and in a specific arrangement may be 2.6 mm.

It is noted that the dimensions presented above relate to a 1 ml syringe and they may be scaled for use with other capacity syringes.

The plunger shaft 104 has a non-circular cross section over some or all of its length. The portion of the plunger shaft 106 having a non-circular cross section is termed the keyed portion of the plunger rod 100. The cross sectional shape of the keyed portion is configured to engage with a correspondingly shaped aperture (a keyed aperture) in the syringe to prevent rotation of the plunger rod 100, as discussed below. In exemplary arrangements, the cross sectional shape of the keyed portion comprises opposed flat edges and opposed outwardly curving edges, giving the impression of a slightly compressed square, the sides of which are bulging outwards. The lugs 106a, 106b are aligned with the cross sectional shape of the keyed portion such that the thread engagement surfaces 110a, 110b engage with and/or act upon the thread of the bung at the points during rotation of the plunger rod 100 when the cross sectional shape of the plunger shaft 104 is aligned with the aperture in the syringe. This is discussed in more detail below.

In exemplary arrangements, the plunger rod 100 may comprise an internal thread that is not visible in FIGS. 1a and 1 b. This is discussed in more detail below.

Figure 2:
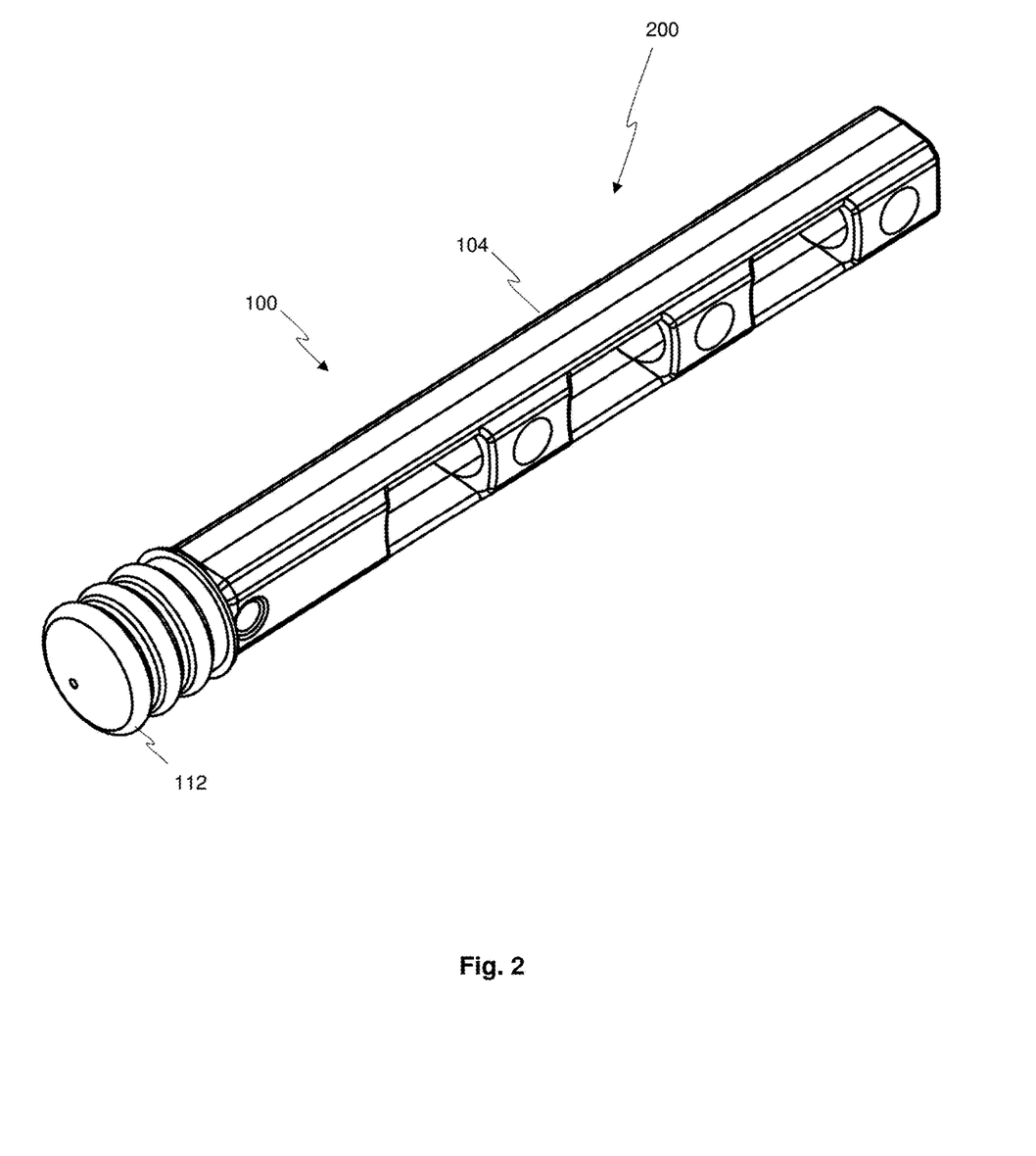
FIG. 2 is an isometric view of a plunger comprising a plunger rod and a bung.

FIG. 2 shows an isometric view of a plunger 200 comprising a plunger rod 100 and a bung 112. The bung fixing 102 (not seen in FIG. 2) is received within a recess in the bung 112.

Figure 3:
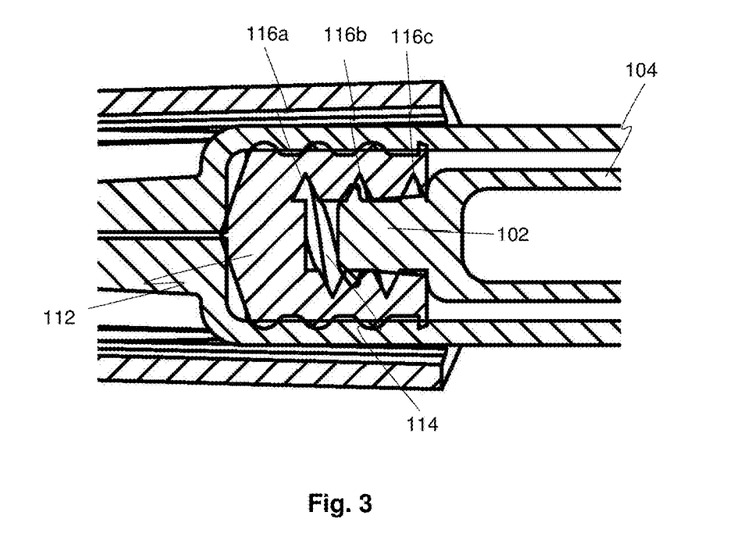
FIG. 3 is a longitudinal section through a needle end of a syringe showing a plunger.

FIG. 3 shows a section view through a needle end of an exemplary syringe to show how the bung fixing 102 of the plunger rod 100 fits within a recess 114 of the bung 112. The lugs 106a, 106b engage with a thread on an internal surface of the recess 114 in the bung 112. The bung fixing 102 of the plunger rod 100 is thereby held within the bung 112.

The recess 114 of the bung 112 comprises a thread comprising a plurality of track portions 116a-c that are adjacent on one side of the recess 114. It is appreciated that there is only a single track taking a helical path, but the portions of the track 116a-c are considered adjacent.

The shoulder 108 abuts an upper surface of the bung 112. The upper surface of the bung 112 is that surface which surrounds the recess 114. As such, further movement of the plunger rod 100 longitudinally into the recess 114 of the bung 112 is resisted. The bung 112 may be formed of a resiliently deformable material, such as a rubberised material. As such, the shoulder 108 resists further longitudinal movement rather than preventing it since further longitudinal movement of the first end 102 of the plunger rod 100 within the recess 107 may be possible if the bung is sufficiently compressed.

The lugs 106a, 106b may contact opposite portions of the track 116a-c of the bung 112 when the plunger rod 100 is coupled with the bung 112 or one lug 106a, 106b may contact a track portion while the other lug 106a, 106b is at a point between track portions.

Figure 4:
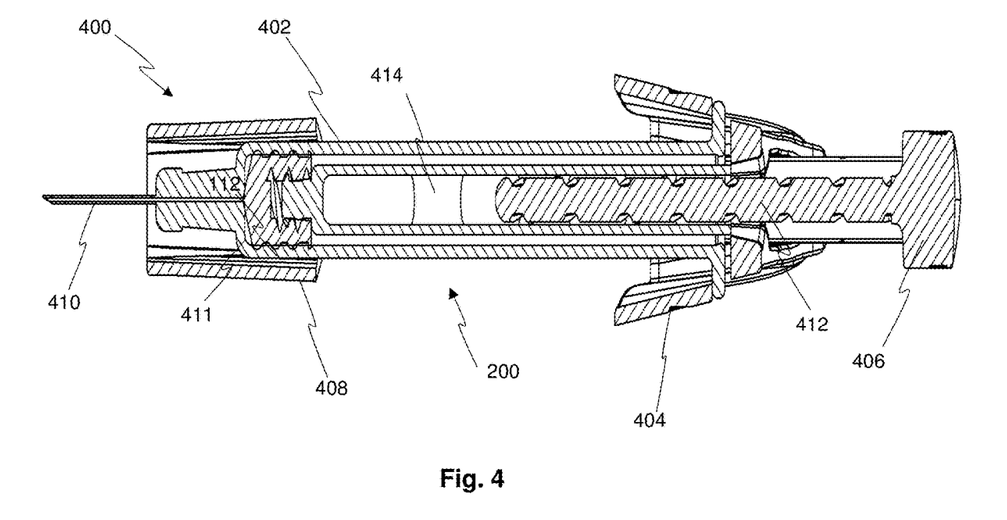
FIG. 4 is a cross section through a syringe.

FIG. 4 shows a cross section of an exemplary syringe 400 comprising a plunger 200, which may comprise features shown in FIGS. 1 to 3.

The exemplary syringe 400 further comprises a barrel 402 into which the plunger 200 is received. A mouth of the barrel 402, through which the plunger 200 is received, includes a keyed aperture corresponding to the cross section of the keyed portion of the plunger shaft 104. As such, the plunger rod 100 is prevented from rotating by the engagement of the keyed portion in the keyed aperture. In the exemplary arrangement of FIG. 4, the keyed aperture at the mouth of the barrel 402 is provided within a handle 404 of the syringe. The handle 404 is shown in more detail in FIGS. 5a and 5b and is discussed below, but is generally configured to be fixed to the barrel 402 and to receive the index and middle fingers of a user of the syringe during use.

The syringe 400 is configured such that after the keyed portion of the plunger rod 100 has passed through the keyed aperture, the plunger rod 100 is free to rotate relative to the barrel 402 and the bung 112. In a particular exemplary arrangement, the plunger rod 100 is configured to pass entirely through the keyed aperture. The length of the plunger rod 100 is configured such that the bung 112 is compressed by the shoulder 108 before the keyed portion passes through the keyed aperture.

The exemplary syringe 400 shown in FIG. 4 further comprises a safety plunger 406 and a sheath 408. The plunger 200 is termed a syringe plunger for description of FIG. 4 in order to differentiate it from the safety plunger 406. The syringe plunger 200 is positioned inside the barrel 402 of the syringe 400 and is configured to move therein. The syringe plunger 200 may move on an inward stroke wherein the syringe plunger 200 moves further into the barrel 402 to expel a substance, or an outward stroke wherein the syringe plunger 200 is drawn out of the barrel 402. A hypodermic needle 410 is fitted to an end 411 of the barrel 402 and is configured to allow the substance to be expelled therefrom.

The safety plunger 406 is coupled to the sheath 408 and to the syringe plunger 200. Therefore, and as explained below, movement of the safety plunger 406 causes movement of the sheath 408 and the safety plunger 200. In the exemplary arrangement of FIG. 4, the coupling between the safety plunger 406, sheath 408 and syringe plunger 200 results in the same amount of longitudinal movement of each, in that they move together.

The coupling of the safety plunger 406 to the syringe plunger 200 is provided by a threaded insert 412 that is received within a correspondingly threaded opening 414 in the syringe plunger 200. The threaded insert 412 is prevented from acting on the thread of the opening 414 and rotating the syringe plunger 200 by the engagement of the keyed portion of the syringe plunger 200 with the keyed aperture. The syringe 400 is configured such that the safety plunger 406 decouples from the syringe plunger 200 at a point on the inward stroke thereof. Longitudinal decoupling is provided by the keyed portion of the syringe plunger 200 passing through the keyed aperture, after which the threaded insert 412 acts upon the thread in the opening 414 to rotate the plunger rod 100 with respect to the barrel 402 and the bung 112. Decoupling therefore allows independent longitudinal movement of the safety plunger 406 and the syringe plunger 200. The term "decoupled" as used herein may encompass any situation in which relative motion is permitted between component parts. In specific component parts, the relative motion may be relative longitudinal motion. This applies to all apparatus disclosed herein. That is, a plunger rod does not need to be detached or separated from a safety plunger in order to be decoupled from it.

The rotation of the plunger rod 100 rotates the bung fixing 102 in the recess 114 of the bung 112 and the lugs 106a, 106b therefore engage with the threaded portion 116b of the internal thread of the bung 112, as described herein.

Continued movement of the safety plunger 406 after decoupling allows movement of the sheath 408 over the needle 410.

Figure 5:
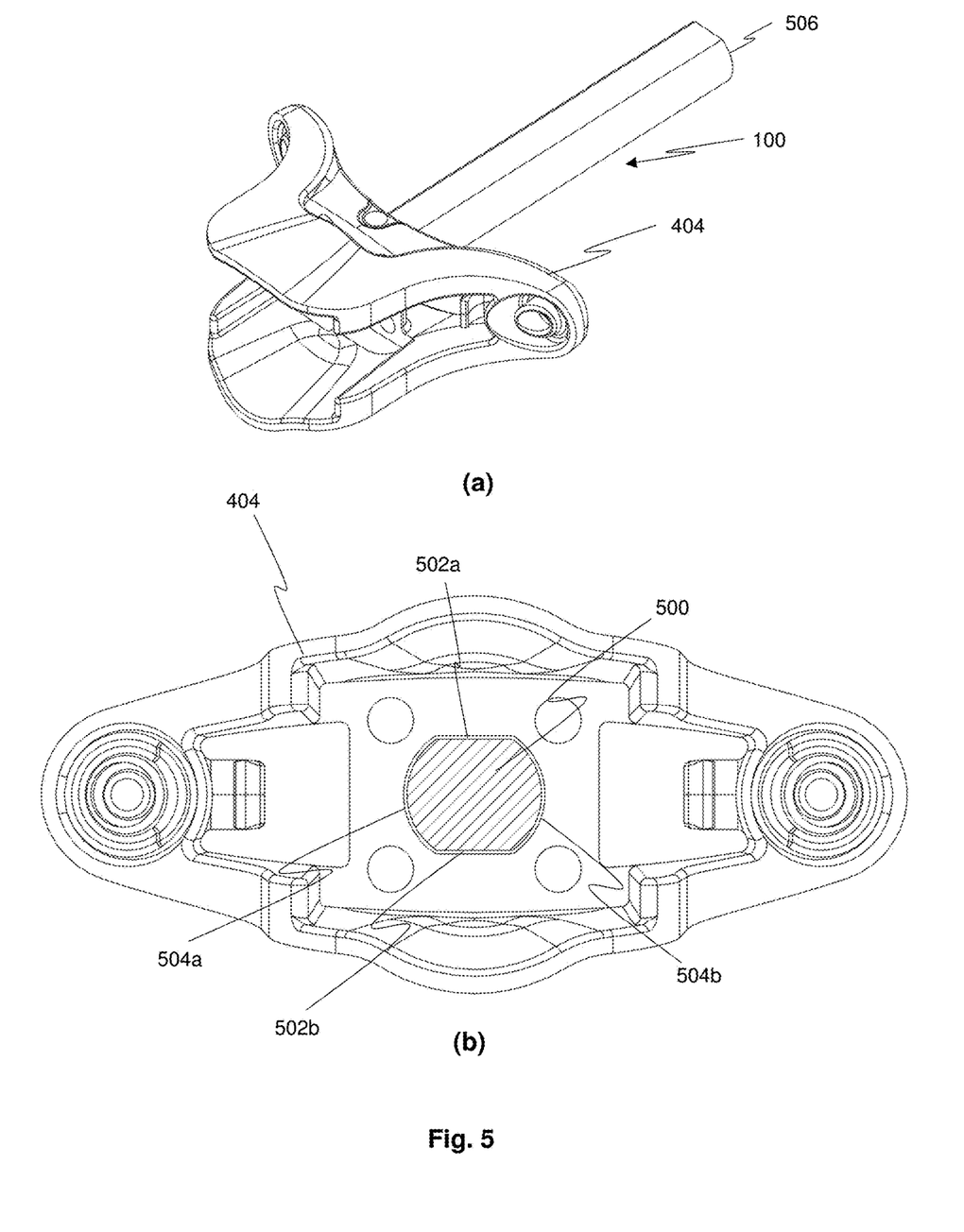
FIG. 5a is an isometric view of a handle portion of a syringe.
FIG. 5b is a plan view of a handle portion of a syringe.

FIG. 5a shows an isometric view of a handle 404 of a syringe 400 with a plunger rod 100 passing therethrough. FIG. 5b shows a plan view of the handle 404. As shown in FIG. 5b, the keyed aperture 500 has opposed straight edges 502a, 502b and opposed outwardly curved edges 504a, 504b. The plunger rod 100 has a corresponding cross section over the keyed portion, as can be seen in FIG. 5a. The opposed straight edges 502a, 502b prevent rotation of the plunger rod 100 when the keyed portion is engaged with the keyed aperture 500. As can be seen in FIG. 5a, the keyed portion of the plunger rod extends all the way to a head end 506. Therefore, the plunger rod 100 is able to pass completely through the keyed aperture 500.

Figure 6:
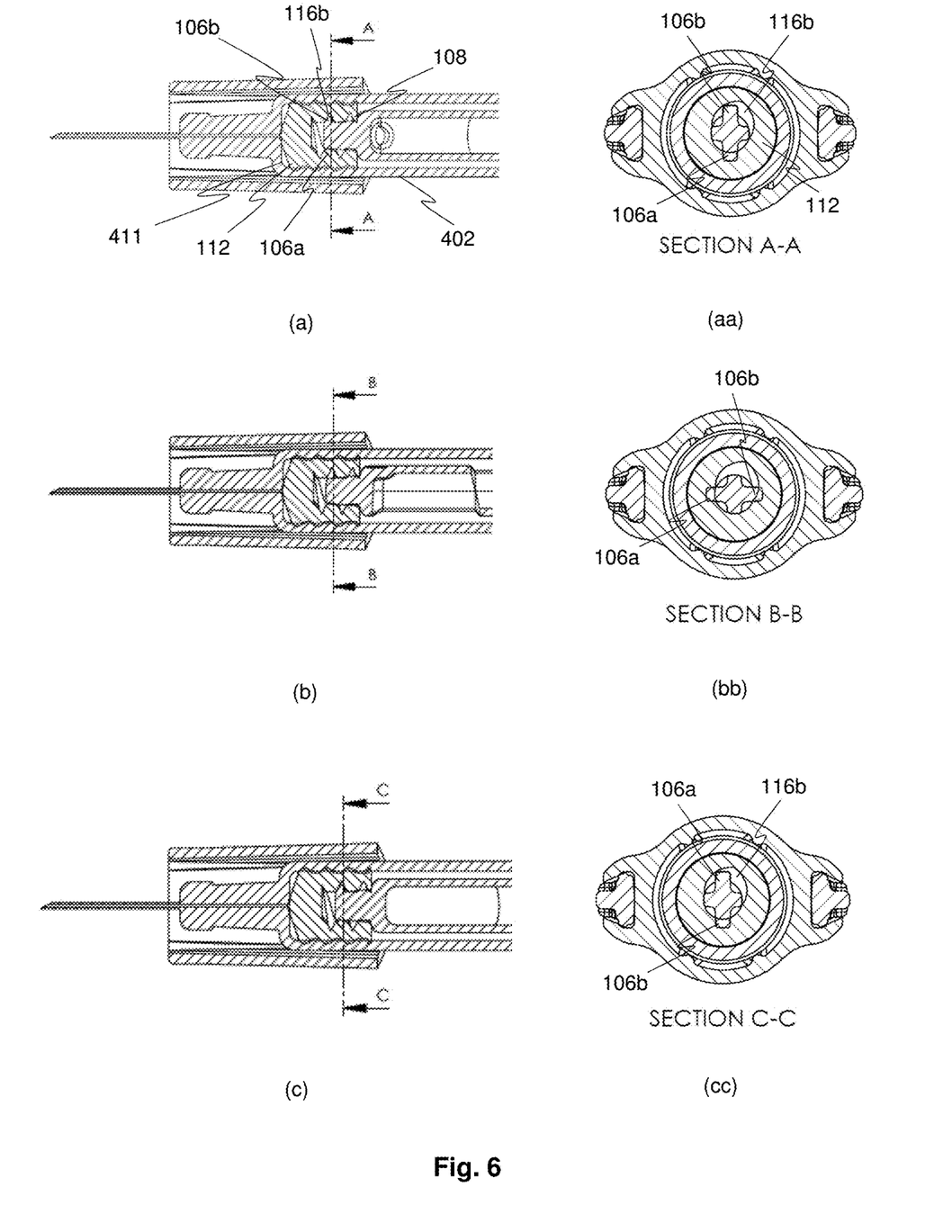

FIGS. 6a-c show sections through the syringe 400 at a number of angles of rotation of the plunger rod 100 following longitudinal decoupling from the safety plunger 406.

FIGS. 6a and 6aa show the position of the plunger rod 100 on completion of the inward stroke of the plunger 200 and before any rotation of the plunger rod 100 relative to the bung 112. The plunger rod 100 has passed through the aperture 500 and the keyed portion of the plunger rod 100 is no longer engaged with the keyed aperture 500. Therefore, the plunger rod 100 is free to rotate relative to the bung 112.

The bung 112 has been placed in a compressed state between the shoulder 108 of the plunger rod 100, which abuts a surface of the bung 112 surrounding the recess 114, and an end 411 of the syringe barrel 402, and the plunger rod 100 and the safety plunger 406 are longitudinally decoupled.

At this point, the keyed portion of the plunger rod 100 is aligned with the keyed aperture 500 and, in the exemplary syringe 400, further force applied to the safety plunger 406 by a user will cause the threaded insert 412 to act upon the thread of the opening 414 to rotate the plunger rod 100 within the barrel 402 of the syringe 400.

As can be seen in FIGS. 6a and 6aa, the thread engagement surface 110b of the lug 106b is engaged with the track portion 116b of the internal thread of the bung 112. The opposite lug 106a has crossed the internal thread of the bung 112 and is not engaged with a track portion. In other arrangements, the opposite lug 106a may be engaged with an opposite track portion of the thread.

As mentioned above, the bung 112 is placed under compression before the plunger rod 100 and the safety plunger 406 decouple. The bung 112 is held under compression at most points during the rotation of the plunger rod 100 by the misalignment of the keyed portion of the plunger rod 100 and the keyed aperture 500. That is, the force applied to the shoulder 108 of the plunger rod 100 by the compressed bung 112 to push the plunger rod 100 "outwards" is resisted by the handle 404, due to the misalignment of the keyed portion and keyed aperture 500.

It will be appreciated, however, that that during a single, 360° rotation of the plunger rod 100, at one or more points, the keyed portion of the plunger rod 100 will align with the keyed aperture 500. For example, during a single rotation of the exemplary plunger rod 100, the alignment occurs at two points on the rotation of the plunger rod 100: at a rotation of 180° and 0°/360°. As such, the bung 112 cannot be held in a compressed state due to misalignment at all points on the rotation of the plunger rod 100. Without a further means of holding the bung 112 in compression the force applied to the shoulder 108 of the plunger rod 100 by the bung 112 would push the plunger rod 100 back through the keyed aperture 500. Such outward movement of the plunger rod 100 may be in the range from 0.25 mm to 0.75 mm.

The lugs 106a-b of the plunger rod 100 are positioned such that at least one lug, 104a or 104b, is configured to engage with the thread of the bung 112 to hold the bung 112 in compression and/or to act on the thread to redistribute the energy stored in the bung at the angles of rotation of the plunger rod 100 at which the keyed portion aligns with the keyed aperture 500.

It will be appreciated that the number and alignment of lugs and the arrangement of the lugs about the bung fixing 102 of the plunger rod 100 is dependent on the cross section of the keyed portion and how many times during a single 360° rotation the keyed portion aligns with the keyed aperture 500. As such, the arrangement and number of lugs used for the purpose of this example is for illustrative purposes only and is not limiting.

FIGS. 6b and 6bb show the engagement of the plunger rod 100 with the bung 112 at a rotation of 90° following decoupling. In this position, the keyed portion and the keyed aperture 500 are misaligned and, as such, it is not necessary for a lugs 106a-b to engage the thread of the bung 112 in order to hold the bung in compression.

The lugs 106a, 106b are configured such that they will cross the internal thread of the bung 112 under a torque applied by the user's thumb through the threaded insert 412 acting upon the thread in the opening 414 of the plunger rod 100. The torque is generated by a linear force of approximately 12 N applied by the user. The material from which the track of the thread of the bung 112 is manufactured also contributes to torque required for the lug to cross the thread. Therefore, the thread and the lug are configured together to ensure that the lug crosses the thread under a torque applied by the user. In the exemplary arrangements disclosed herein, the shoulder 108 of the plunger rod 100 resists further motion of the bung fixing 102 into the recess 114 in the bung 112. This prevents continued travel of the bung fixing within the track portion of the thread such that the lugs 106a, b cross the thread under the torque applied by the user.

In FIGS. 6b and 6bb, the lugs 106a-b have crossed the thread of the bung. The keyed portion is misaligned with the keyed aperture 500 and so the bung is held in compression by the handle 404.

In FIGS. 6c and 6cc the plunger rod has rotated a further 90° from the position in FIGS. 6b and 6bb to 180°. The keyed portion of the plunger rod 100 is aligned with the keyed aperture 500 of the handle 404. As such, the plunger rod may be forced outwards from the keyed aperture 500 under the force applied by the compressed bung 112. If this were allowed to happen then this movement would be felt by the user as the safety plunger 406 is depressed after longitudinal decoupling from the syringe plunger 200 during deployment of the sheath. The movement would be felt as a judder in the movement of the safety plunger 406 as the plunger rod 100 becomes momentarily engaged with the keyed aperture 500.

The lug 106a has now crossed into the track portion 116b of the thread and the thread engagement surface 110a is engaged with that track portion of the thread. This provides a compressive force on the bung 112 to hold it in compression and resist its expansion to force the plunger rod 100 into the keyed aperture 500. Alternatively, or in addition, the lug 106b is acting on the track portion 116b of the thread under a torque applied to the plunger rod 100 by the user. Acting on the thread means that the torque applied to the plunger rod 100 is translated into linear motion of the bung 112 by the movement of the lug 106a along the track portion 116b of the thread. This linear motion acts to pinch or compress the portion of the bung above the track portion 116b between the lug 106a and the shoulder 108. This has the effect of relieving the stored energy in the bulk of the bung 112 below the track portion 116b. That is, the compression of the portion of the bung 112 above the track portion 116b allows expansion of the portion of the bung 112 below the track portion 116b. As a result, the bung 112 does not expand to force the plunger rod 100 into the keyed aperture 500. This is a redistribution of the energy stored in the bung 112.

As the keyed portion of the plunger rod 100 rotates further such that it is misaligned with the keyed aperture 500, the lug 106a overcomes and crosses the thread. Exemplary plunger rods described herein therefore allow for relative rotation of the plunger rod with respect to the bung without the bung fixing being threaded into the recess of the bung and without the energy stored in the bung forcing the plunger rod out of the keyed aperture when the two are aligned. As will be appreciated, the same principles apply to the lug 106b when the plunger rod 100 has rotated by a further 180°.

Exemplary lugs may cross the thread into adjacent track portions 116a and 116c during the rotation of the plunger rod 100.

The skilled person will be able to envisage other syringes and features thereof without departing from the scope of the appended claims.

The invention claimed is:

1. A plunger comprising a plunger rod for use in a syringe barrel for driving a bung through the syringe barrel to expel a substance therefrom, the plunger comprising:
   a bung including a recess for receiving a bung fixing, the bung including a thread on a sidewall of the recess, the thread including a track portion, and
   the plunger rod including a bung fixing configured to be received within the recess of the bung and comprising first and second laterally extending lugs on opposite sides of the bung fixing, each lug comprising a thread engagement surface angled rearwards from a lateral axis to allow linear motion of each lug through the thread on the bung and configured to engage with a corresponding point on the track portion of the thread of the bung which is on the sidewall of the recess,
   wherein each lug is further configured to cross the thread by overcoming the thread on relative rotation between the plunger rod and the bung under a force applied by a user, such that the thread engagement surface of each lug engages the corresponding point of the track portion every full rotation of the plunger rod relative to the bung.

2. A plunger according to claim 1, wherein each lug is configured to act upon the track portion of the thread before crossing the thread.

3. A plunger according to claim 1, wherein each lug is angularly spaced about a periphery of the bung fixing such that the thread engagement surface of each lug is rotatable to engage the corresponding point of the track portion of the thread.

4. A plunger according to claim 3, wherein the first and second lugs are equally angularly spaced about the periphery.

5. A plunger according to claim 3, wherein each lug is at the same longitudinal position on the plunger rod.

6. A plunger according to claim 1, wherein the first and second lugs are configured such that when the thread engagement surface of the first lug is engaged with the point on the track portion, the thread engagement surface of the second lug engages a point on a further track portion opposite to the track portion.

7. A plunger according to claim 1, further comprising a shoulder configured to abut a surface of the bung surrounding the recess when the bung fixing is received therein, the shoulder being configured to resist further longitudinal movement of the plunger rod into the recess.

8. A plunger according to claim 7, wherein an extension of the bung fixing from the shoulder is such that when the shoulder abuts the surface of the bung surrounding the recess, the bung fixing is not in contact with a bottom surface of the recess.

9. A plunger according to claim 7, wherein each lug is configured to act upon the track portion of the thread before crossing the thread, and wherein the first and second lugs are configured to act on the thread to compress a portion of the bung between the first and second lugs and the shoulder.

10. A plunger according to claim 1, wherein a keyed portion of the plunger rod has a non-circular cross section configured to engage a corresponding keyed aperture of a syringe to prevent rotation of the plunger rod,
   and wherein each lug is positioned such that the thread engagement surface engages the point of the track portion of the thread when the cross section of the plunger rod is aligned with the keyed aperture.

11. A plunger according to claim 10, wherein each lug is configured to act upon the track portion of the thread before crossing the thread, and wherein the first and second lugs are positioned such that they act upon the track portion of the thread when the cross section of the plunger rod is aligned with the keyed aperture.

12. A syringe comprising:
   a plunger according to claim 1.

13. A syringe according to claim 12, wherein a keyed portion of the plunger rod has a non-circular cross section configured to engage a corresponding keyed aperture of a syringe to prevent rotation of the plunger rod,
   wherein each lug is positioned such that the thread engagement surface engages the point of the track portion of the thread when the cross section of the plunger rod is aligned with the keyed aperture, the plunger rod being received within a mouth of a barrel of the syringe such that movement of the plunger within the barrel expels a substance therefrom, and
   wherein the mouth of the barrel comprises the keyed aperture corresponding to the non-circular cross section of the keyed portion of the plunger rod and configured to engage therewith to prevent rotation of the plunger rod relative to the barrel, and wherein, after the keyed portion of the plunger rod has passed through the aperture, the plunger rod is rotatable relative to the barrel and the bung.

14. A syringe according to claim 13, wherein the bung is resiliently deformable and the plunger rod is configured to compress the bung against an end of the barrel as the keyed portion of the plunger rod passes through the keyed aperture in the mouth of the barrel, such that during rotation of the plunger rod, energy is stored in the bung and exerts a force on the plunger rod outwards from the barrel.

15. A syringe according to claim 14, wherein the thread engagement surface of each of the first and second lugs of the plunger rod is configured to engage the point on the track portion of the thread on the sidewall of the bung when the keyed portion of the plunger rod is aligned with the keyed aperture, such that the bung does not expand to force the plunger rod out of the aperture.

16. A syringe according to claim 14, wherein the plunger rod further comprises a shoulder configured to abut a surface of the bung surrounding the recess when the bung fixing is received therein, the shoulder being configured to resist further longitudinal movement of the plunger rod into the recess, wherein each lug is configured to act upon the track portion of the thread before crossing the thread,     wherein the first and second lugs are configured to act on the thread to compress a portion of the bung between the first and second lugs and the shoulder, and     wherein the first and second lugs are configured to act upon the track portion of the thread on the sidewall of the bung to compress a portion of the bung between the first and second lugs and the shoulder of the plunger rod when the keyed portion of the plunger rod is aligned with the keyed aperture.

17. A plunger rod for use in a syringe barrel for driving a bung through the syringe barrel to expel a substance therefrom, the plunger rod comprising:

a bung fixing configured to be received within a recess of the bung and comprising first and second laterally extending lugs on opposite sides of the bung fixing, each lug comprising a thread engagement surface angled rearwards from a lateral axis to allow linear motion of each lug through a thread on the bung and configured to engage with a corresponding point on a track portion of the thread of the bung which is on a sidewall of the recess,     wherein each lug is further configured to cross the thread by overcoming the thread on relative rotation between the plunger rod and the bung under a force applied by a user, such that the thread engagement surface of each lug engages the corresponding point of the track portion every full rotation of the plunger rod relative to the bung,     wherein a keyed portion of the plunger rod has a non-circular cross section configured to engage a corresponding keyed aperture of a syringe to prevent rotation of the plunger rod, and     wherein each lug is positioned such that the thread engagement surface engages the point of the track portion of the thread when the cross section of the plunger rod is aligned with the keyed aperture.

\* \* \* \* \*